United States Patent [19]

Gleason et al.

[11] Patent Number: 5,211,175
[45] Date of Patent: May 18, 1993

[54] METHOD FOR IMPLANTING ELECTRA-ACUPUNCTURE NEEDLE

[75] Inventors: Curtis A. Gleason, Palo Alto; Marshall L. Stoller, San Francisco; Tom F. Lue, Millbrae; Richard A. Schmidt; Emil A. Tanagho, both of San Rafael, all of Calif.

[73] Assignee: Regents of the University of California, Berkeley, Calif.

[21] Appl. No.: 845,211

[22] Filed: Mar. 3, 1992

Related U.S. Application Data

[60] Division of Ser. No. 282,002, Dec. 9, 1988, Pat. No. 5,094,242, which is a continuation-in-part of Ser. No. 268,167, Nov. 7, 1988, abandoned.

[51] Int. Cl.$^5$ .................................................. H61G 5/24
[52] U.S. Cl. .................................... 128/642; 128/422; 128/784; 128/907; 606/189
[58] Field of Search ............... 128/907, 642, 734, 735, 128/419 PG, 419 PT, 420.5, 420.6, 422, 783, 784, 799, 419 R, 419 E, 421, 303.18, 903, 419 G, 419 L, 804; 606/189, 32, 41; 600/30, 26; 604/20

[56] References Cited

U.S. PATENT DOCUMENTS

| | | | |
|---|---|---|---|
| 3,387,434 | 12/1967 | Abell | 128/419 Z |
| 3,943,932 | 3/1976 | Woo | 128/907 |
| 4,161,943 | 2/1979 | Nogier | 606/189 |
| 4,219,027 | 8/1986 | Lund | 128/642 |
| 4,262,672 | 4/1981 | Kief | 606/189 |
| 4,683,896 | 8/1987 | Herbst et al. | 128/642 |
| 4,967,766 | 11/1990 | Bradshaw | 128/642 |
| 5,094,242 | 3/1992 | Gleason et al. | 128/907 |

Primary Examiner—Randall L. Green
Assistant Examiner—K. Reichle
Attorney, Agent, or Firm—Phillips, Moore, Lempio & Finley

[57] ABSTRACT

An electro-acupuncture system comprises a transmitter for emitting high frequency magnetic energy pulses and a receiver, sealed within an implantable "thumb-tack" shaped device, for receiving and converting such pulses into stimulating pulses of current. The device comprises a head having an exposed ring-electrode (anode) secured therein and a needle-like electrode (cathode) having a proximal end secured in the head and a distal end adapted to pierce body tissue. The latter electrode comprises a metallic tube secured in the head and a metallic wire inserted through the tube to position and fix an exposed tip of the wire at a preselected location and depth in the body tissue, in accordance with method steps taught herein.

7 Claims, 3 Drawing Sheets

METHOD FOR IMPLANTING ELECTRA-ACUPUNCTURE NEEDLE

CROSS-REFERENCE TO RELATED APPLICATION

This application is a divisional of U.S. Ser. No. 07/282,002, filed on Dec. 9, 1988, now U.S. Pat. No. 5,094,242, which was a continuation-in-part of U.S. patent application Ser. No. 268,167, filed on Nov. 7, 1988 for "Electro-Acupuncture System With Implantable Needle" now abandoned.

TECHNICAL FIELD

This invention relates generally to a system and method for performing acupuncture and more particularly to a system having an implantable device for receiving and converting high frequency magnetic energy pulses to stimulating pulses of current to selectively stimulate body tissue.

BACKGROUND OF THE INVENTION

Acupuncture, practiced in Eastern medicine for thousands of years, is time-tested and has proven effective. For example, acupuncture has proven very effective in the treatment of numerous types of headaches, including myogenic headaches. Results of such treatments were published by Jensen, L. B., Tallgreen, A., Trost, T., and Jensen, S. V. in the *Scandinavian Journal of Dental Research*, Vol. 85, pp. 456–470, 1977. In addition, acupuncture has proven very effective in the treatment of non-myogenic headaches, such as migraine headaches. This use was discussed in the *American Journal of Acupuncture*, Vol. 14, No. 2, 1986. Acupuncture has also proven effective for relieving pain during labor. For example, this treatment proved effective in 66–70% of the patients treated in China, as reported by McIntyre, J.W.R. in the article entitled "Observation on practice of anesthesia in the Peoples Republic of China," published in *Anesthesia and Analgesia*, Vol. 53, pp 107–111, 1984.

However, acupuncture is not limited to painful disease processes. It is also very effective in treating many functional disorders, as with patients attempting to stop smoking. Results of such treatments were published in *Chinese Acupuncture and Moxibustion*, Vol. 6, No. 5, October 1986. In addition, acupuncture has potential applications to other significant problems, such as schizophrenia. The treatment of five hundred cases of schizophrenia with the application of acupuncture had a cure rate of 55%, as reported in *Chinese Acupuncture and Moxibustion*, Vol. 5, No. 4, August 1985. Other functional problems successfully treated by use of acupuncture are discussed in the following articles: Pruritus (*American Journal of Acupuncture*, Vol. 14, No. 3, July 1986); "Improvement of Sperm Characteristics in Subfertile Men" (*Singapore Journal of Obstetrics and Gynecology*, Vol. 16, No. 3, Nov. 1985); and "Alcoholic Rehabilitation" (*American Journal of Acupuncture*, Vol. 12, No. 2, April 1984). Acupuncture is indeed a modality that has proven successful, when applied to many and varied disease processes.

SUMMARY OF THE INVENTION

An object to this invention is to provide an improved electro-acupuncture system and method, including a device adapted to be subcutaneously implanted in body tissue for intermittent stimulation of the tissue by an external transmitter.

The device comprises a head defining a cavity at an upper side thereof, a receiver mounted in the head for selectively receiving and converting high frequency magnetic energy pulses into stimulating pulses, a first electrode having its proximal end extending into the cavity defined in the head and connected to the receiver for transmitting the stimulating pulses to the needle's distal end, an adhesive in the form of a plug filling the cavity to secure the proximal end of the first electrode in the head and to fix the distal end of the first electrode at a preselected location in the body tissue, and a second electrode secured to the head and connected to the receiver for receiving the stimulating pulses from the distal end of the first electrode after they have passed through the body tissue.

In another aspect of this invention, the first electrode comprises a metallic tube secured in the head and a metallic wire inserted through the tube whereby the wire can be reciprocated in the tube to place its exposed tip at said preselected location In another aspect of this invention, method steps are taught for surgically implanting the device in body tissue.

BRIEF DESCRIPTION OF THE DRAWINGS

Other objects and advantages of this invention will become apparent from the following description and accompanying drawings wherein.

DESCRIPTION OF THE PREFERRED EMBODIMENTS

GENERAL DESCRIPTION

Clinical studies, utilizing pigtailed monkeys, have demonstrated that acupuncture needles placed at the Sin Yin Chiao point (SP-6), approximately three-finger breaths cephalad to the medial malleolus, can dramatically reduce or eliminate inappropriate bladder contractions This has recently been confirmed in human studies. Needles placed at random locations had no effect. Needles placed in locally anesthetized hind limbs also had no therapeutic effects, suggesting . that an intact nerve supply is mandatory.

Detailed studies have demonstrated that electrical stimulation of sacral efferents at S2 and S3 can modulate bladder function in a human. It is possible that placement of needles at the Sin Yin Chiao point stimulate the sacral afferent nerves. In this way, the same sacral nerve circuitry is affected. Stimulation of both the sacral afferent and efferent nerves results in plantar flexion of the great toe. This confirms accurate placement of the needle. Such application of acupuncture needles at various loci may be utilized for other pain and non-painful disease processes.

Figure 2:
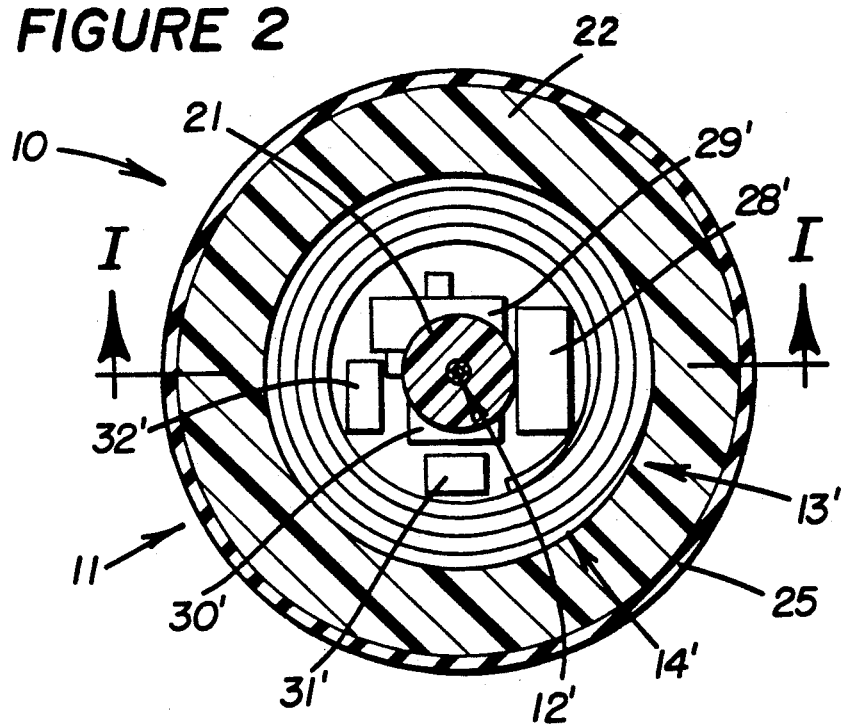
FIG. 2 is cross-sectional view through the device, taken in a direction of arrows II—II in FIG. 1.
Figure 1:
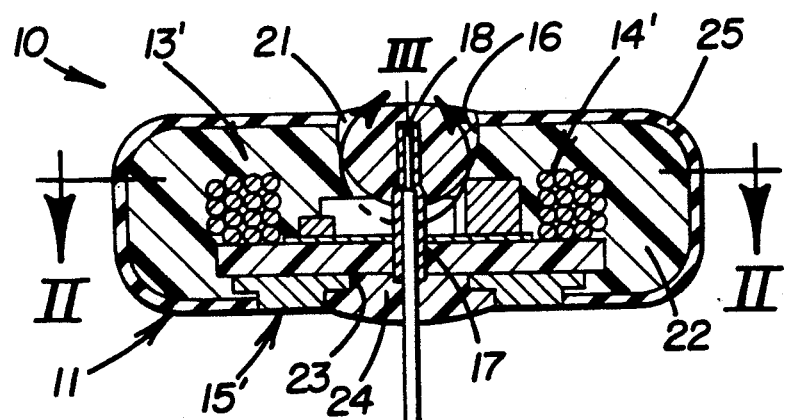
FIG. 1 is longitudinal sectional view of an electro-acupuncture device adapted to be subcutaneously implanted in body tissue, the view being taken in direction of arrows I—I in FIG. 2.
Figure 3:
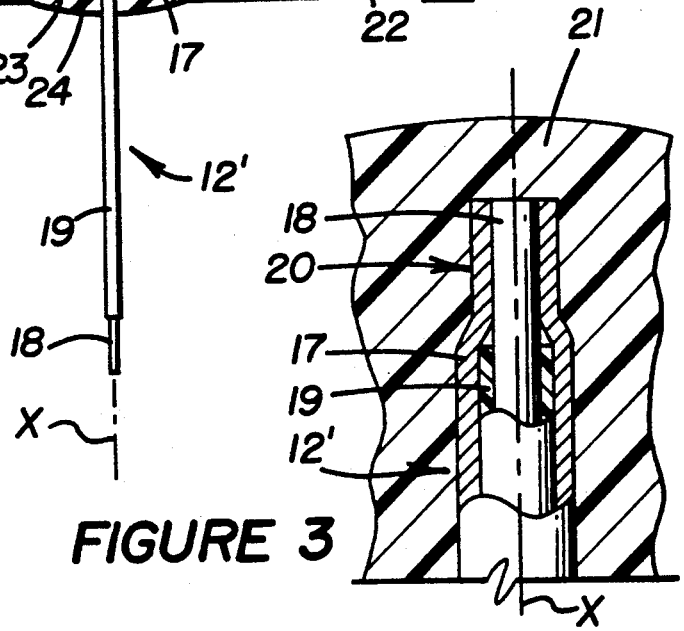
FIG. 3 is enlarged sectional view, generally taken within circular arrow III in FIG. 1.
Figure 4:
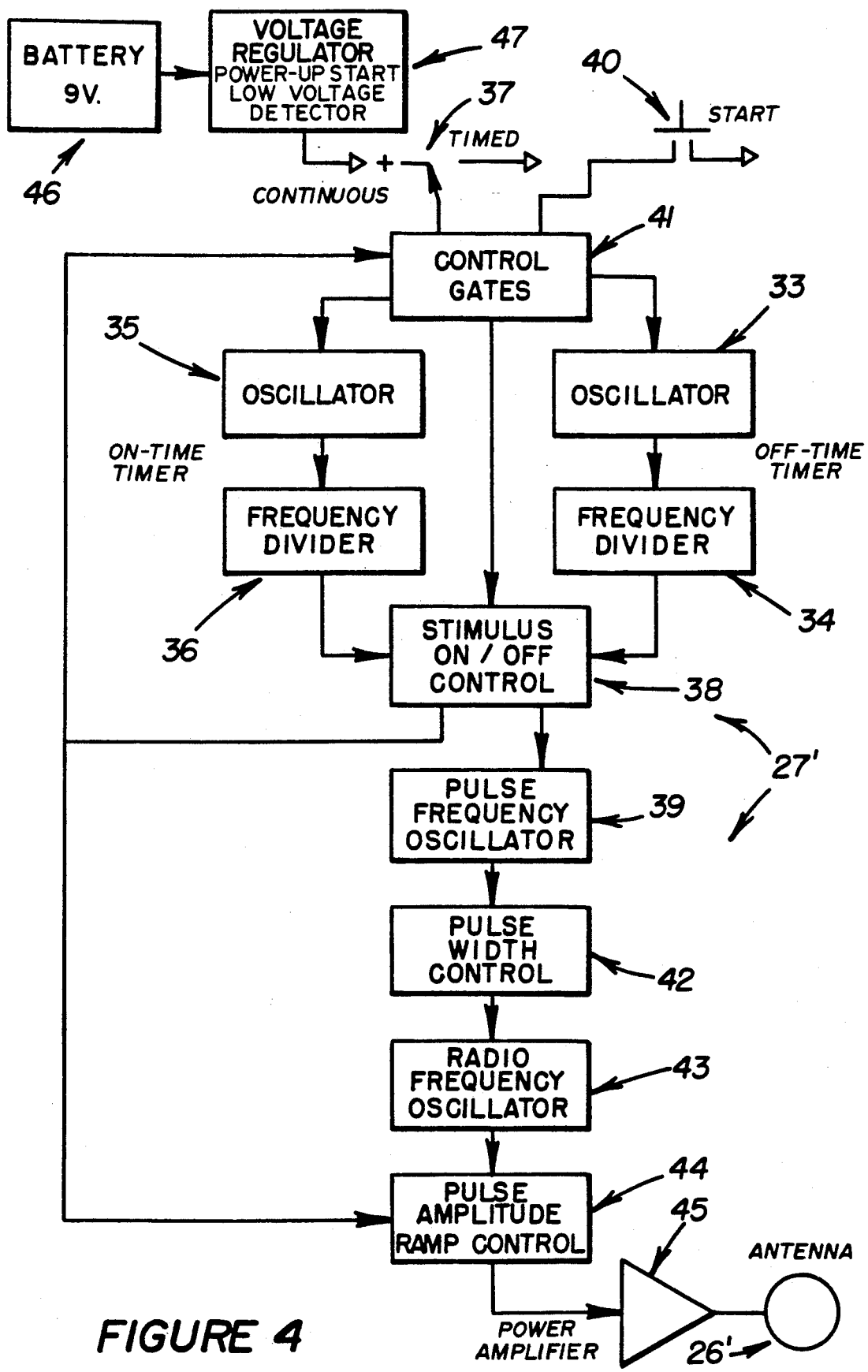
FIG. 4 schematically illustrates an electronic circuit for an external transmitter associated with an electronic receiver contained in the device of FIGS. 1—3.

Components of the system shown in FIGS. 1-5, corresponding to components disclosed in applicants' above-referenced parent application, are like-numbered and accompanied by a prime symbol ('). FIGS. 1-3 illustrate an implantable electro-acupuncture device 10 for stimulating body tissue by use of a pair of electrodes 12' and 15'. Such stimulation occurs in response to high frequency magnetic energy pulses received by a coil 14' of a receiver 13' from an antenna 26' of an external transmitter 27'. (FIG. 4). Needle-like electrode 12' and ring-like electrode 15' functionally correspond to electrodes 12 and 15, described in applicants' above-referenced parent application.

As described hereinafter, the device is designed for pre-testing to determine a preselected and optimum location for the device and the precise position of the tip of its emitting electrode in body tissue Further, implantation of the device in a human requires minimal surgical dissection. After pre-testing and location of the appropriate loci, utilizing skin impedance, resistance and capacitive reactance, a small incision is made to create a small subcutaneous pouch for the device Thus, repeated office visits for repetitive percutaneous needle punctures can be eliminated. This procedure reduces the likelihood of infection, hemorrhage, and possible injury to nearby structures with repeated punctures. The implanted device will allow the patient to perform self treatment at varied time intervals, depending upon the patient's symptomatology Receiver 13' is sealed in a head 11 of device 10 to convert radio frequency signals to electrical output stimulating pulses with a small voltage, variable frequencies up to 50 cps, and a pulse width less than 1.0 msec.

DETAILED DESCRIPTION

Referring the FIGS. 1-3, device 10, shown readied for surgical implantation, is disposed on a central longitudinal axis X and has the general shape of a "thumbtack." Annular head 11, centered on the axis, has a centrally disposed cavity 16 defined at an upper side thereof. As described more fully hereinafter, first electrode 12' comprises a metallic (stainless-steel) tube 17 and a needle-like metallic (platinum-irridium) wire 18, having a standard dielectric and bio-compatible insulation 19 coated thereon.

The tube and wire are disposed on axis X and have their proximal ends positioned in cavity 16. The tube is preferably crimped at 20 to electrically connect the tube and wire together, either by piercing insulation 19 or after the proximal end of the wire has been stripped of insulation, as shown in FIG. 3. Alternatively, the proximal ends of the tube and wire could be soldered to each other.

After the tube has been connected to the wire, cavity 16 is filled with a plug 21, composed of a liquid dielectric and bio-compatible adhesive material that is allowed to solidify. As described below, this novel installation and connection of first electrode 12' to head 11 facilitates pre-testing of a patient to precisely fix an exposed tip of the electrode at a pre-selected location and depth in body tissue. In particular, prior to applying crimp 20 and plug 21, wire 18 can be reciprocated in tube 17 to precisely ascertain such location. The wire is then cut to size and the crimp and plug are formed, as shown.

Receiver 13' is of the type described in applicants' above-referenced application and includes inductive coil 14'60 mounted and sealed within head 11. The receiver selectively receives and converts high frequency magnetic energy pulses from antenna 26' of transmitter 27' (FIG. 4) into stimulating pulses. Tube 17 is electrically connected to one side of the receiver (FIG. 5) for receiving and transmitting the stimulating pulses to the exposed tip of electrode 12'.

Metallic (gold-plated titanium) ring 15' is connected to the opposite side of the receiver and is secured to a bottom side of the head to expose an outer side thereof to the exposed tip of electrode 12' (cathode). The ring functions as a second electrode (anode) whereby stimulating pulses will be sequentially emitted from the exposed tip of the needle, passed through the body tissue, and received by the ring. A body of dielectric insulating material 22, such as a suitable epoxy, substantially encapsulates coil 14' and other component parts of receiver 13', described more fully hereinafter.

Ring 15' underlies the coil and other components of the receiver and defines an annular cavity 23 therein, adjacent to the bottom side of head The ring is substantially encapsulated by insulating material 22 to firmly retain the ring and receiver within the head. A second plug 24, composed of a dielectric and bio-compatible insulating material, fills cavity 23 to secure a distal end of tube 17 to the head and to aid in electrically insulating electrode 12' from ring electrode 15'. A coating of dielectric and bio-compatible material forms a cover 25 substantially over head 11 to expose the outer side of ring electrode 15', the tip of electrode 12', and plugs 21 and 24, exteriorly of device 10.

The material composing cover 25 and plugs 21 and 24 may constitute a standard bio-compatible polyurethane material (e.g., Bioflex) or medical grade Silastic which is a composition in physical character comparable to milled and compounded rubber prior to vulcanization, but containing organosilicon polymers Components fabricated from the latter material are serviceable from −73° to +160° C., retain good physical and dielectric properties when placed in a patient, and exhibit excellent resistance to compression set, weathering, and corona. In addition, thermal conductivity of this material is high and water absorption is low.

Figure 5:
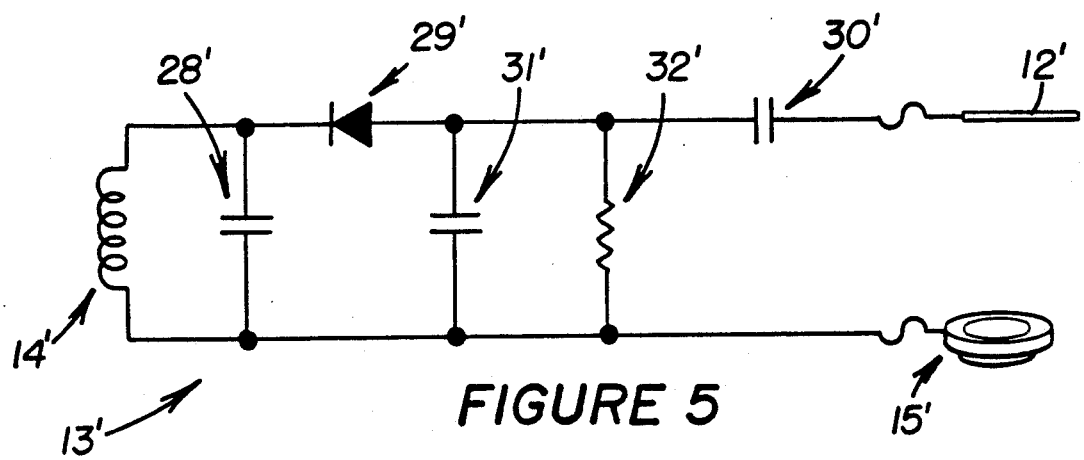
FIG. 5 schematically illustrates the electronic receiver.

Referring to FIGS. 4 and 5, receiver 13' functions to convert pulsed magnetic energy received from an antenna 26' of a transmitter 27' (FIG. 4) into current pulses which are directed to the stimulus site via electrode 12' In FIG. 5, identical numerals (accompanied with a prime symbol) depict component parts corresponding to component parts of the receiver described in applicants above-referenced parent application. The receiver is miniaturized in accordance with standard techniques to render device 10 as small as possible so that it can be easily implanted with a minimal amount of tissue displacement. The device must be of such a size and configuration that it will remain stable and will not migrate within the tissue over time.

As described in applicants+ parent application, the net charge transfer between the tissue and the electrodes must be zero so that tissue in the vicinity of the electrodes is not damaged by charge buildup. Otherwise stated, the product of the current magnitude and the duration of current in one direction must equal the product of the current magnitude and the duration of current in the other direction. A suitable electrical configuration and circuitry that accomplishes the above desiderata is shown in FIG. 5.

Antenna 26' of stimulus generator and transmitter 27' (FIG. 4) transmits the pulsed alternating magnetic field to receiver 13' whereat the stimulus pulses are detected by coil 14' and transmitted to the stimulus site. Coil 14', when exposed to the magnetic field of transmitter antenna 26', converts the changing magnetic field into corresponding voltages with alternating polarity between the coil ends.

As shown in FIG. 5, a capacitor 28' may be used to tune coil 14' to the high-frequency of the transmitter. The capacitor increases the sensitivity and the selectivity of the receiver. With the capacitor, the receiver is made sensitive to frequencies near the resonant frequency of the tuned circuit and less sensitive to frequencies away from the resonant frequency.

A diode 29' allows the current that is produced by the alternating voltage of the coil to pass in one direction only. This current path includes diode 29', a capacitor 30', standard electrode leads, electrode 12' and the body tissue. A capacitor 31' and resistor 32' filter-out the high-frequency component of the receiver signal and thereby leave a current pulse of the same duration as the bursts of the high-frequency signal.

Capacitor 30' blocks any net direct current so that the net charge transferred to the tissue is zero. Alternatively, charge builds-up one way on the capacitor as current passes through the tissue and, when the high-frequency burst is completed and the voltage across capacitor 31' and resistor 32' becomes zero, capacitor 30' discharges and thus causes the current in the tissue to reverse. This current reversal during the interval between stimulus pulses reverses the charge that was formerly built-up in the tissue during the stimulus current.

The circuit components are soldered in a conventional manner to an upper conductive layer on a printed circuit board (FIG. 1). Gold-plated titanium electrode ring 15' is soldered to the circuit board and conductive "holes" are formed therethrough to connect the appropriate circuit components to the ring, as shown schematically in FIG. 5. Tube 17 is placed at the center of the coil, on axis X, and is suitably soldered in place.

Wire 18 of electrode 12' is electrically insulated by insulation 19, except at its proximal end connection to tube 17 and at its exposed tip so that no current leakage occurs along the needle-like electrode. The stimulating current is thus concentrated at the exposed tip (cathode) of the wire and ring 15' will serve as the return electrode (anode). The area of the ring's outer side, exposed to the tissue, is substantially larger than the needle tip so that the current density is too low to unduly stimulate tissue that is in contact with the ring.

The compact construction of head 11 stabilizes device 10 when it is implanted under the skin. As described more fully hereinafter, the head is placed under the skin and over the subcutaneous tissue with the needle piercing downwardly into the tissue and adjacent to the acupuncture stimulus site. The length of the needle is adjusted by cutting it to the desired length. When it is cut, insulation 19 is stripped at the distal end of the needle stimulating current.

Typical values for the components of receiver 13, (FIG. 5) to achieve a transmitter high-frequency of 2.85 MHz are Inductive coil 14' (15 turns, 0.30 in. diameter); Capacitor 28' (1,800 pfd); Capacitor 31' (1,000 pfd); Capacitor 30' (0.22 ufd); and Resistor 32' (10,000 ohms).

FIG. 4 schematically illustrates a typical circuit comprising external, battery-powered stimulus generator and transmitter 27'. The circuit produces radio-frequency pulses that are coupled to implanted receiver 13' (FIG. 5) via antenna 26' when it is placed over the site of the receiver. The receiver converts these radio-frequency pulses into stimulus pulses and directs them to the stimulus site.

Generator-transmitter 27' contains two timing circuits, associated control circuits, the stimulus pulse generator and radio-frequency circuits One of the timing circuits controls the time that the stimulation is being generated (the ON-TIME timer, 35 and 36 and the other timing circuit controls the time that the stimulation is off (the OFF-TIME timer, 33 and 34. Thus, these timers produce a cyclic on and off stimulus pattern to the stimulus site A selector switch 37 is used by a patient to select the continuous mode or the timed mode. In the continuous mode, a stimulus ON/OFF Control 38 enables a pulse frequency oscillator 39 to run continuously In the timed mode, stimulus ON/OFF control 38 alternately turns pulse frequency oscillator 39 on and off. The on and off times are controlled by the ON-TIME timer 35 and 36 OFF-TIME timer 33, 34, respectively. A Start switch 40 is used to restart pulse frequency oscillator 39 at any time that this oscillator is in the off-time period Control gates 41 are logic circuits that gate time oscillators 33 and 35 on and off alternately, when switch is in the timed mode. These logic circuits also disable both timer oscillators 33 and 35, but keep pulse frequency occillators 39 on when the continuous mode is selected Both timers consist of oscillators 33, 35 and frequency dividers 34, 36. Variable times are obtained by varying the oscillator frequency and by selecting the outputs of periods from a few seconds to over an hour can be readily reduced by this arrangement.

The actual stimulus pulse is produced by pulse frequency oscillator 39 and a pulse width control 42. The frequency of the stimulus pulse is determined by pulse frequency oscillator 39 and can be set between one pulse per second to about 100 pulses per second. The width of the stimulus pulse is controlled by the pulse width control and be varied between 50 microseconds and 500 microseconds.

Each brief pulse from pulse width control 42 turns a radio-frequency oscillator 43 on. Hence, bursts of radio-frequency energy are produced for the duration of the stimulus pulse width. A pulse amplitude ramp control 44 produces a ramping increase in the pulse amplitudes at the start of the on-time period. Thus, the stimulus pulses are not applied abruptly to the stimulus site By ramping the amplitude, the stimulus is applied gradually and hence a more comfortable sensation is experienced by the patient. A power amplifier 45 amplifies the bursts of radio-frequency pulses and sends them to antenna 26' for transmission to the implanted receiver.

The generator-transmitter is powered by a standard nine-volt battery 46 which supplies energy to a voltage regulator and detector 47. The voltage regulator maintains a constant voltage of five volts to the other circuits even while the battery voltage decreases from nine volts to six volts. The low-voltage detector illuminates a light-emitting-diode (not shown) when the battery voltage drops below six and one-half volts to indicate that the battery should be replaced. A standard power-up start circuit sets stimulus ON/OFF control 38 to turn-on pulse frequency oscillator 39 so that the stimulus pulses are on when the stimulator is first turned on.

Standard COSMOS integrated circuits are used for the logic, control and timing circuits: Control gates 41 (CD4001, CD4011, CD4069); gate time oscillators 33,35 (CD4011); frequency dividers 34,36 (CD4020); stimulus ON/OFF control 38 (CD4013); pulse frequency oscillator 39 and pulse width control 42 (CD4011). Standard bipolar transistors are used in radio-frequency oscillator 43, pulse amplitude ramp control 44, and power amplifier 45. A standard voltage regulator is used in low-voltage detector 47.

SURGICAL PROCEDURE AND METHOD FOR IMPLANTING DEVICE 10

One surgical procedure includes the following steps. Needle or wire 18 (FIG. 1) is stripped of its insulation 19 at its distal end and the needle is pierced into the skin of a patient at a previously determined acupuncture site. Alternatively, a bare needle (without insulation 19) could be used. The cathode (−) of a standard stimulus pulse generator (e.g. Urodynamic Systems, Inc. Direct Nerve Stimulator Model No. URYS 800) is attached to the needle and the anode (+) of the pulse generator is connected to a conductive pad secured on the skin of the patient. The acupuncture point is stimulated following standard acupuncture procedures to verify the correct placement and depth of the stimulating needle.

A local anesthetic is injected subcutaneously at the acupuncture site so that a small incision can be made, without pain, in the skin at the site of the needle. An incision of about fifteen millimeters, centered on the needle, will expose a subcutaneous implant site. Appropriate clamps or forceps are used to hold the needle at the desired depth into the stimulation site.

The stimulus pulse generator is then disconnected from the needle. An appropriate amount of medical grade silastic in "jelly" form is injected into cavity 23 to form plug 24. While holding the needle in position, tube 17 is aligned and slid onto needle 18 and head 11 is moved toward the exposed implant site. Plug 24 is sufficiently soft, before solidification, to permit the needle to pierce it and to slide upwardly into the tube. The needle is regrasped above the head and while, holding the needle steady, the head is moved fully into the implant site.

Using a pair of pliers, tube 17 is crimped at 17' (FIG. 3) onto the needle so that the tube secures the needle in place and makes electrical contact therewith. The portion of the needle extending above the tube is then cut-off An appropriate amount of medical grade silastic is then injected into cavity 16 to form plug 21, insulating electrode 12' from the body tissue The incision is closed and sutured over the implanted device and the device is tested with the acupuncture transmitter (FIG. 4) by placing transmitter coil or antenna 26' over the implanted receiver site.

I claim:

1. A method for applying an electro-acupuncture device to body tissue, said device comprising a head having receiver means therein for selectively receiving and converting high frequency magnetic energy pulses into stimulating pulses, a first electrode including a metallic tube electrically connected to said receiver means for receiving said stimulating pulses therefrom and a needle-like wire adapted to be slidably mounted in said tube, and a second electrode, electrically connected to said receiver means and electrically insulated from said tube, said method comprising the steps of
    placing said head on said body tissue,
    inserting said wire through said tube to project beyond a distal end of said tube to pierce said body tissue,
    positioning an exposed tip at a distal end of said wire at a preselected distance from the distal end of said tube and at a at a preselected location and depth in said body tissue,
    electrically connecting said needle to said tube and fixing the position on the exposed tip of said wire in said body tissue,
    transmitting high frequency magnetic energy pulses to said receiver means to convert said energy pulses to stimulating pulses, and
    transmitting said stimulating pulses sequentially from said receiver means to said first electrode, through said body tissue and to said second electrode.

2. The method of claim 1 further comprising, prior to said connecting step, pre-testing for said preselected location by reciprocating said wire in said tube to move the exposed tip of said wire to varying depths in said body tissue and periodically transmitting high frequency magnetic energy pulses to said receiving means, converting said energy pulses to stimulating pulses, and transmitting said stimulating pulses to said wire, through said body tissue and to said second electrode to ascertain said preselected location.

3. The method of claim 1 further comprising exposing proximal ends of said tube and said wire within a cavity defined on an upper side of said head, prior to said connecting step, and then electrically connecting said wire to said tube to permit transmission of said stimulating pulses from said tube and through said wire and filling said cavity with an adhesive to form a plug securing said wire and said tube within said head.

4. The method of claim 1 wherein said connecting step comprises crimping said tube to said wire to permit transmission of said stimulating pulses from said tube and through said wire.

5. The method of claim 1 further comprising surgically implanting said device in said body tissue and selectively transmitting said energy pulses to said receiver means from externally of said body tissue to convert said energy pulses into said stimulating pulses.

6. A method for implanting an electro-acupuncture device in body tissue, said device comprising receiver means for selectively receiving and converting high frequency magnetic energy pulses into stimulating pulses, first electrode means in the form of a needle electrically connected to said receiver means for receiving said stimulating pulses therefrom, and second electrode means electrically connected to said receiver means for receiving said stimulating pulses from said first electrode means after they have passed through body tissue, said method comprising the steps of
    determining an acupuncture point on a person,
    verifying said acupuncture point,
    incising tissue of said person at said acupuncture point to form an incision exposing a subcutaneous implant side,
    implanting said device to place a distal end of said needle at said implant site,
    closing said incision,
    transmitting high frequency magnetic energy pulses to said receiver means to convert said energy pulses to stimulating pulses, and sequentially transmitting said stimulating pulses from said receiver means to said first electrode means, through said tissue and to said second electrode means.

7. The method of claim 6 wherein said determining step comprises determining said acupuncture point to be at the Sin Yin Chiao point, approximately three-finger breadths cephalad to the medial malleolus of said person.

* * * * *